(12) United States Patent
Owens et al.

(10) Patent No.: US 9,999,637 B2
(45) Date of Patent: Jun. 19, 2018

(54) FUNCTIONALIZED TISSUE MATRICES

(71) Applicant: LifeCell Corporation, Branchburg, NJ (US)

(72) Inventors: Rick T. Owens, Stewartsville, NJ (US); Zhigang Liu, Hillsborough, NJ (US)

(73) Assignee: LifeCell Corporation, Branchburg, NJ (US)

( * ) Notice: Subject to any disclaimer, the term of this patent is extended or adjusted under 35 U.S.C. 154(b) by 0 days. days.

(21) Appl. No.: 13/865,629

(22) Filed: Apr. 18, 2013

(65) Prior Publication Data
US 2013/0280223 A1    Oct. 24, 2013

Related U.S. Application Data

(60) Provisional application No. 61/637,413, filed on Apr. 24, 2012.

(51) Int. Cl.

| | | |
|---|---|---|
| A61K 35/12 | (2015.01) | |
| A61K 31/7088 | (2006.01) | |
| A61K 38/16 | (2006.01) | |
| A61K 38/48 | (2006.01) | |
| A61K 38/50 | (2006.01) | |
| A61K 45/06 | (2006.01) | |
| A61L 27/36 | (2006.01) | |

(52) U.S. Cl.
CPC .......... *A61K 35/12* (2013.01); *A61K 31/7088* (2013.01); *A61K 38/16* (2013.01); *A61K 38/4886* (2013.01); *A61K 38/50* (2013.01); *A61K 45/06* (2013.01); *A61L 27/362* (2013.01); *A61L 27/3687* (2013.01)

(58) Field of Classification Search
None
See application file for complete search history.

(56) References Cited

U.S. PATENT DOCUMENTS

| | | |
|---|---|---|
| 4,347,841 A | 9/1982 | Benyo et al. |
| 4,350,629 A | 9/1982 | Yannas et al. |
| 4,352,883 A | 10/1982 | Lim |
| 4,776,173 A | 10/1988 | Kamarei et al. |
| 4,796,603 A | 1/1989 | Dahlke et al. |
| 4,854,316 A | 8/1989 | Davis |
| 5,256,140 A | 10/1993 | Fallick |
| 5,439,684 A | 8/1995 | Prewett et al. |
| 5,634,931 A | 6/1997 | Kugel |
| 5,648,330 A | 7/1997 | Pierschbacher et al. |
| 5,695,998 A | 12/1997 | Badylak et al. |
| 5,712,252 A | 1/1998 | Smith |
| 5,780,295 A | 7/1998 | Livesey et al. |
| 5,880,242 A | 3/1999 | Hu et al. |
| 5,942,496 A | 8/1999 | Bonadio et al. |
| 5,972,007 A | 10/1999 | Sheffield et al. |
| 6,132,986 A | 10/2000 | Pathak et al. |
| 6,166,288 A | 12/2000 | Diamond et al. |
| 6,174,320 B1 | 1/2001 | Kugel et al. |
| 6,197,036 B1 | 3/2001 | Tripp et al. |
| 6,231,608 B1 | 5/2001 | Stone |
| 6,258,125 B1 | 7/2001 | Paul et al. |
| 6,381,026 B1 | 4/2002 | Schiff et al. |
| 6,554,863 B2 | 4/2003 | Paul et al. |
| 6,599,318 B1 | 7/2003 | Gabbay |
| 6,610,006 B1 | 8/2003 | Amid et al. |
| 6,638,284 B1 | 10/2003 | Rousseau et al. |
| 6,652,593 B2 | 11/2003 | Boyer, II et al. |
| 6,726,660 B2 | 4/2004 | Hessel et al. |
| 6,767,369 B2 | 7/2004 | Boyer, II et al. |
| 6,776,800 B2 | 8/2004 | Boyer, II et al. |
| 6,790,213 B2 | 9/2004 | Cherok et al. |
| 6,833,408 B2 | 12/2004 | Sehl et al. |
| 7,105,001 B2 | 9/2006 | Mandelbaum |
| 7,235,295 B2 | 6/2007 | Laurencin et al. |
| 7,815,561 B2 | 10/2010 | Forman et al. |
| 8,323,352 B2 | 12/2012 | Friedman et al. |
| 8,333,803 B2 | 12/2012 | Park et al. |

(Continued)

FOREIGN PATENT DOCUMENTS

| | | |
|---|---|---|
| WO | WO-2000/16822 A1 | 3/2000 |
| WO | WO-2000/47114 A1 | 8/2000 |

(Continued)

OTHER PUBLICATIONS

Belyansky, et al. (Dec. 2011) "The Addition of Lysostaphin Dramatically Improves Survival, Protects Porcine Biomesh from Infection, and Improves Graft Tensile Shear Strength", Journal of Surgical Research, 171: 409-15.*
Corbin, et al. (2008) "Metal Chelation and Inhibition of Bacterial Growth in Tissue Abscesses", Science, 319(5865): 962-65.*
Mc Devitt, et al. (2011) "A Molecular Mechanism for Bacterial Susceptibility to Zinc", PLoS Pathogens, 7(11): e1002357 (pp. 1-9).*
Dennis O'Neil (downloaded Mar. 7, 2015) "Primates: Overview", http://anthro.palomar.edu/primate/prim_1.htm, No journal, no volume, no issue, no page numbers, Published by Palomar Community College, San Marcos, CA, 6 pages long.*
http://www.anatomy.org/content/how-many-organs-no-matter-how-minor-it-does-human-being-have-and-what-are-they, (2014, downloaded Mar. 7, 2015), unknown author, by the American Association of Anatomists, Bethesda, Maryland, USA, no journal, no issue, no volume, no page numbers, 3 pages long.*
Bozym, et al. (Jun. 1, 2010) "Free zinc ions outside a narrow concentration range are toxic to a variety of cells in vitro", Experimental Biological Medicine, 235(6): 741-50 (published as pp. 1-20 online).*
Ahn et al., "The past, present, and future of xenotransplantation" *Yonsei Med J.*, 45(6):1017-1024 (Dec. 31, 2004).
Allman et al., "Xenogeneic Extracellular Matrix Grafts Elicit a TH2-Restricted Immune Response" *Transplantation*, 71(11):1631-1640 (Jun. 15, 2001).

(Continued)

*Primary Examiner* — Robert M Kelly
(74) *Attorney, Agent, or Firm* — McCarter & English, LLP (57) ABSTRACT

Disclosed herein are tissue treatment products that have been bound to at least one chelating agent. Also disclosed are tissue treatment products that have been functionalized with at least one metal and/or at least one metal-binding protein. The tissue treatment products can have antimicrobial properties and/or factors that promote or enhance native cell migration, proliferation, and/or revascularization after implantation into a subject. Also disclosed are methods of making and using the tissue treatment products. The tissue treatment products can be implanted into a tissue in need of repair, regeneration, healing, treatment, and/or alteration and can promote or enhance native cell migration, proliferation, and/or revascularization.

28 Claims, 4 Drawing Sheets

(56) References Cited

U.S. PATENT DOCUMENTS

| | | | |
|---|---|---|---|
| 2002/0055143 | A1 | 5/2002 | Bell et al. |
| 2002/0061328 | A1 | 5/2002 | Gertzman et al. |
| 2002/0082697 | A1 | 6/2002 | Damien |
| 2002/0099344 | A1 | 7/2002 | Hessel et al. |
| 2002/0120347 | A1 | 8/2002 | Boyer, II et al. |
| 2002/0197242 | A1 | 12/2002 | Gertzman et al. |
| 2003/0009235 | A1 | 1/2003 | Manrique et al. |
| 2003/0039678 | A1 | 2/2003 | Stone et al. |
| 2004/0059364 | A1 | 3/2004 | Gaskins et al. |
| 2004/0078077 | A1 | 4/2004 | Binette et al. |
| 2004/0078089 | A1 | 4/2004 | Ellis et al. |
| 2005/0008672 | A1 | 1/2005 | Winterbottom et al. |
| 2005/0009178 | A1 | 1/2005 | Yost et al. |
| 2005/0028228 | A1 | 2/2005 | McQuillan et al. |
| 2005/0043716 | A1 | 2/2005 | Frimer |
| 2005/0054771 | A1 | 3/2005 | Sehl et al. |
| 2005/0058629 | A1 | 3/2005 | Harmon et al. |
| 2005/0118230 | A1 | 6/2005 | Hill et al. |
| 2005/0288691 | A1 | 12/2005 | Leiboff |
| 2006/0105026 | A1 | 5/2006 | Fortune et al. |
| 2006/0106419 | A1 | 5/2006 | Gingras |
| 2006/0115515 | A1 | 6/2006 | Pirhonen et al. |
| 2006/0247206 | A1 | 11/2006 | Feins |
| 2006/0276908 | A1 | 12/2006 | Sogaard-Andersen et al. |
| 2007/0009586 | A1 | 1/2007 | Cohen et al. |
| 2007/0111937 | A1 | 5/2007 | Pickar et al. |
| 2007/0202173 | A1 | 8/2007 | Cueto-Garcia |
| 2007/0293878 | A1 | 12/2007 | Butsch |
| 2008/0033461 | A1 | 2/2008 | Koeckerling et al. |
| 2008/0071300 | A1 | 3/2008 | Popadiuk et al. |
| 2008/0091277 | A1 | 4/2008 | Deusch et al. |
| 2008/0095819 | A1 | 4/2008 | Gourdie et al. |
| 2008/0113035 | A1 | 5/2008 | Hunter |
| 2008/0131509 | A1 | 6/2008 | Hossainy et al. |
| 2008/0147199 | A1 | 6/2008 | Yost et al. |
| 2008/0167729 | A1 | 7/2008 | Nelson et al. |
| 2009/0130221 | A1 | 5/2009 | Bolland et al. |
| 2010/0221237 | A1 | 9/2010 | Kokai-Kun et al. |
| 2011/0044968 | A1 | 2/2011 | Bolotin et al. |
| 2011/0135703 | A1 | 6/2011 | Shipp |

FOREIGN PATENT DOCUMENTS

| | | |
|---|---|---|
| WO | WO-2003/017826 A2 | 3/2003 |
| WO | WO-2003/032735 A1 | 4/2003 |
| WO | WO-2005/009134 A1 | 2/2005 |
| WO | WO-2007/043513 A1 | 4/2007 |
| WO | WO-2007/134134 A2 | 11/2007 |
| WO | WO-2009/009620 A2 | 1/2009 |
| WO | WO-2010/019753 A2 | 2/2010 |
| WO | WO-2010/078353 A2 | 7/2010 |
| WO | WO-2012/142419 A1 | 10/2012 |
| WO | WO-2012/166784 A1 | 12/2012 |

OTHER PUBLICATIONS

Aycock et al., "Parastomal Hernia Repair With Acellular Dermal Matrix" *J. Wound Ostomy Continence Nurs.*, 34(5):521-523 (2007).

Badylak et al., "Endothelial cell adherence to small intestinal submucosa: An acellular bioscaffold" *Biomaterials*, 20:2257-2263 (1999).

Badylak et al., "Extracellular Matrix as a Biological Scaffold Material: Structure and Function" *Acta Biomaterialia*, 5(1):1-13 (2009).

Beniker et al., "The use of acellular dermal matrix as a scaffold for periosteum replacement" *Orthopedics*, 26(5 Suppl):s591-s596 (May 2003).

Bruder et al., "The Effect of Implants Loaded with Autologous Mesenchymal Stem Cells on the Healing of Canine Segmental Bone Defects" *J. Bone Joint Surg.*, 80:985-986 (1998).

Buma et al., "Tissue engineering of the meniscus" *Biomaterials*, 25(9):1523-1532 (2004).

Chaplin et al., "Use of an Acellular Dermal Allograft for Dural Replacement: An Experimental Study" *Neurosurgery*, 45(2):320-327 (Aug. 1999).

Chen et al. "Acellular Collagen Matrix as a Possible 'Off the Shelf' Biomaterial for Urethral Repair" *Urology*, 54(3):407-410 (1999).

Collins et al., "Cardiac xenografts between primate species provide evidence for the importance of the α-galactosyl determinant in hyperacute rejection" *J. Immunol.*, 154:5500-5510 (1995).

Costantino et al., "Human Dural Replacement With Acellular Dermis: Clinical Results and a Review of the Literature" *Head & Neck*, 22:765-771 (Dec. 2000).

Dobrin et al., "Elastase, collagenase, and the biaxial elastic properties of dog carotid artery" *Am. J. Physiol. Heart Circ. Physiol.*, 247:H124-H131 (1984).

Edel, "The use of a connective tissue graft for closure over an immediate implant covered with occlusive membrane" *Clin. Oral Implants Res.*, 6:60-65 (1995) (Abstract).

Fowler et al., "Ridge Preservation Utilizing an Acellular Dermal Allograft and Demineralized Freeze-Dried Bone Allograft: Part II. Immediate Endosseous Impact Placement" *J. Periodontol.*, 71:1360-1364 (2000).

Fowler et al., "Root Coverage with an Acellular Dermal Allograft: A Three-Month Case Report" *J. Contemp. Dental Pract.*, 1(3):1-8 (2000).

Galili et al., "Man, Apes, and Old World Monkeys Differ from Other Mammals in the Expression of α-Galactosyl Epitopes on Nucleated Cells" *J. Biol. Chem.*, 263(33):17755-17762 (1988).

Galili et al., "Interaction Between Human Natural Anti-α-Galactosyl Immunoglobulin G and Bacteria of the Human Flora" *Infect. Immun.*, 56(7):1730-1737 (1988).

Galili et al., "Interaction of the Natural Anti-Gal Antibody with α-Galactosyl Epitopes: a Major Obstacle for Xenotransplantation in Humans" *Immunology Today*, 14(10):480-482 (1993).

Gamba et al. "Experimental abdominal wall defect repaired with acellular matrix" *Pediatr. Surg. Int.*, 18:327-331 (2002).

Gebhart et al., "A radiographical and biomechanical study of demineralized bone matrix implanted into a bone defect of rat femurs with and without bone marrow" *Acta Orthop. Belg.*, 57(2):130-143 (1991) (Abstract).

Hammond et al., "Parastomal Hernia Prevention Using a Novel Collagen Implant: A Randomised Controlled Phase 1 Study" *Hernia*, 12:475-481 (2008).

Kish et al., "Acellular Dermal Matrix (AlloDerm): New Material in the Repair of Stoma Site Hernias" *The American Surgeon*, 71:1047-1050 (Dec. 2005).

Kridel et al., "Septal Perforation Repair with Acellular Human Dermal Allograft" *Arch. Otolaryngol. Head Neck Surg.*, 124:73-78 (Jan. 1998).

Laidlaw et al., "Tympanic Membrane Repair With a Dermal Allograft" *Laryngoscope*, 111:702-707 (Apr. 2001).

Lee et al., "In vitro evaluation of a poly(lactide-co-glycolide)-collagen composite scaffold for bone regeneration" *Biomaterials*, 27:3466-3472 (2006).

Lu et al., "Novel Porous Aortic Elastin and Collagen Scaffolds for Tissue Engineering" *Biomaterials*, 25(22):5227-5237 (2004).

Simon et al., "Early failure of the tissue engineered porcine heart valve Synergraft™ in pediatric patients" *Eur. J. Cardiothorac. Surg.*, 23(6):1002-1006 (2003).

Zheng et al. "Porcine small intestine submucosa (SIS) is not an acellular collagenous matrix and contains porcine DNA: Possible implications in human implantation" *J. Biomed. Mater. Res. B: Appl. Biomater.*, 73(1):61-67 (2005).

Akyol et al., "Outcome of the patients with chronic mesh infection following open inguinal hernia repair," *J. Korean Surg. Soc.* 84 (2013) 287-291 at 289.

Guanatillake et al., "Biodegradable Synthetic Polymers for Tissue Engineering," *Eur. Cells and Materials* 5 (2003) 1-16.

\* cited by examiner

FUNCTIONALIZED TISSUE MATRICES

This application claims priority to U.S. Provisional Application No. 61/637,413, filed Apr. 24, 2012, which is incorporated herein by reference in its entirety.

The present disclosure relates generally to methods of making and using tissue treatment products comprising a structural scaffold and chelating agents, which may be bound to metals and/or metal-binding proteins.

Various products are currently used to repair, regenerate, heal, or otherwise treat diseased or damaged tissues and organs. These products can include intact tissue grafts and/or partially or completely decellularized tissues. Such materials provide a collagen-rich scaffold into which native cells from surrounding cells can migrate and proliferate, thereby promoting or enhancing repair, regeneration, or treatment. Implantation of foreign materials, however, including foreign tissue materials, brings with it the potential to introduce undesirable microbial contamination to the implant site. Furthermore, although implanted materials can be coated in various bioactive substances to help promote or enhance tissue repair, regeneration or treatment, those bioactive substances may diffuse out of the implanted material, thereby reducing or eliminating their beneficial effects.

Accordingly, disclosed herein are tissue treatment products comprising acellular tissue matrices and/or other synthetic materials that are bound to one or more chelating agents, metals, and/or metal-binding proteins. The tissue treatment product can serve as a platform for the rapid and flexible attachment of one or more chelating agents and/or metals, such as zinc or copper, that provide antimicrobial properties and/or serve as a binding site for one or more metalloenzymes or metal-binding proteins having desirable properties. The tissue treatment products that are bound to one or more chelating agents, metals, and/or metal-binding proteins can be implanted into a tissue in need of repair, regeneration, and/or treatment. For example, the tissue treatment products can be implanted in any tissue that has been separated by disease, trauma or surgery, or following the surgical removal of bulk tissue, or as an implant for cosmetic purposes.

In various embodiments, a tissue treatment product is disclosed, comprising a porous material having a natural or artificial scaffold, wherein the porous material comprises at least one of the following materials: an extracellular matrix of a partially decellularized tissue, an extracellular matrix of a completely decellularized tissue, and a porous synthetic scaffold material; and wherein at least one chelating agent is covalently bound to the porous material. In some embodiments, the tissue treatment product comprises at least one of a hyaluronic acid derivative, chitosan, polycaprolactone, polyglycolide, polylactide, polydioxane, a polyether ester, poly(lactide-co-glycolide), and/or polyhydroxyalkonate. In certain embodiments, the tissue treatment product comprises a polyurethane material. In other embodiments, the tissue treatment product comprises the extracellular matrix of a partially or completely decellularized tissue selected from at least one of human, nonhuman primate, pig, cow, horse, goat, sheep, dog, cat, rabbit, guinea pig, gerbil, hamster, rat, and mouse tissue, or from at least one of bone, skin, dermis, intestine, vascular, urinary bladder, tendon, ligament, muscle, fascia, neurologic tissue, vessel, liver, heart, lung, kidney, and cartilage tissue.

In certain embodiments, the tissue treatment product further comprises one or more viable cells, such as mammalian cells (e.g., stem cells). In some embodiments, the tissue treatment product further comprises at least one factor selected from an anti-inflammatory agent, an analgesic, a cell growth factor, an angiogenic factor, a differentiation factor, a cytokine, a hormone, and a chemokine.

In various embodiments, at least one chelating agent is covalently bound to free amine, thiol, or hydroxyl groups on the porous material in the tissue treatment product. In certain embodiments, the at least one chelating agent is at least one of iminodiacetic acid (IDA), nitrilotriacetic acid (NTA), ethylenediaminetetraacetic acid (EDTA), and/or diethylenetriaminepentaacetic acid (DTPA). In some embodiments, the chelating agent is covalently bound to the porous material in the tissue treatment product via an activating agent (e.g. N-hydroxysulfosuccinimide (NHS), suberic acid bis (N-hydroxysuccinimide ester), 1,4-butanediol diglycidyl ether, epibromohydrin, and/or 1,2,7,8-diepoxyoctane).

In various embodiments, a tissue treatment product is functionalized with at least one metal that is bound to the at least one chelating agent on the tissue treatment product. In some embodiments, the at least one metal comprises at least one of calcium, zinc, copper, silver, cobalt, nickel, manganese, and/or magnesium. In certain embodiments, the at least one metal has antimicrobial properties and/or the ability to interact with at least one metal-binding protein.

In various embodiments, a tissue treatment product is functionalized with at least one metal and/or at least one metal-binding protein that binds the metal on the tissue treatment product. In some embodiments, the at least one metal-binding protein has antimicrobial properties (e.g., lysostaphin). In some embodiments, the at least one metal-binding protein comprises at least one matrix metalloproteinase, such as a collagenase, gelatinase, stromolysin, matrilysin, and/or elastase.

In various embodiments, a kit is provided, comprising a tissue treatment product, as disclosed herein, and instructions for using the kit. In some embodiments, the kit is packaged under aseptic or sterile conditions.

In various embodiments, a method of making a tissue treatment product is provided, comprising selecting a porous material having a natural or artificial scaffold, wherein the material comprises at least one of the following materials: an extracellular matrix of a partially decellularized tissue, an extracellular matrix of a completely decellularized tissue, and a porous synthetic scaffold material; and covalently binding at least one chelating agent to the porous material. In some embodiments, covalently binding at least one chelating agent to the porous material comprises first reacting the chelating agent with an activating agent (such as N-hydroxysulfosuccinimide (NHS), suberic acid bis(N-hydroxysuccinimide ester), 1,4-butanediol diglycidyl ether, epibromohydrin, and/or 1,2,7,8-diepoxyoctane) and then covalently binding the activated chelating agent to free amine, thiol, or hydroxyl groups on the porous material. In some embodiments, the at least one chelating agent comprises at least one of IDA, NTA, EDTA, and/or DTPA.

In various embodiments, a method of making a tissue treatment product further comprises functionalizing the tissue treatment product by contacting the tissue treatment product with at least one metal (e.g., calcium, zinc, copper, silver, cobalt, manganese, nickel, and/or magnesium) that can bind to the one or more chelating agents on the tissue treatment product. In certain embodiments, the at least one metal has antimicrobial properties and/or the ability to interact with at least one metal-binding protein.

In various embodiments, a method of making a tissue treatment product further comprises contacting the functionalized tissue treatment product with at least one metal-binding protein. In some embodiments, the at least one metal-binding protein has antimicrobial properties (e.g., lysostaphin). In some embodiments, the at least one metal-binding protein comprises at least one matrix metalloproteinase such as a collagenase, gelatinase, stromolysin, matrilysin, and/or elastase.

In some embodiments, a method of making a tissue treatment product further comprises irradiating the tissue treatment product, for example with 15-25 kGy E-beam irradiation.

In various embodiments, a method of treatment is provided, comprising implanting a tissue treatment product into a tissue in need of repair, regeneration, healing, treatment, and/or alteration. In some embodiments, the implanted tissue treatment product provides a structural scaffold into which native cells from surrounding tissue can migrate and proliferate, thereby promoting or enhancing tissue repair, regeneration, healing, treatment, and/or alteration. In certain embodiments, the chelating agent(s) on a tissue treatment product can bind and sequester at least one undesirable metal at the site of implantation. In certain embodiments, the implanted tissue treatment product is functionalized with at least one metal and has a lower level of bioburden, as compared to an implanted tissue treatment product that is not functionalized with metal, at any point in time following implantation into a host tissue. In some embodiments, the implanted tissue treatment product is functionalized with at least one metal and at least one metal-binding protein, and the implanted tissue treatment product has lower level of bioburden, as compared to an implanted tissue treatment product that is not functionalized with the metal-binding protein, at any point in time following implantation into a host tissue. In certain embodiments, the implanted tissue treatment product is functionalized with at least one metal and at least one matrix metalloproteinase, and the matrix metalloproteinase promotes and/or enhances native cell proliferation, migration, differentiation, and/or angiogenesis, and/or reduces inflammation at the site of implantation, as compared to an implanted tissue treatment product that is not functionalized with a matrix metalloproteinase.

In some embodiments, a tissue treatment product is implanted for cosmetic purposes, for example, for use in combination with a breast implant. In other embodiments, a tissue treatment product is implanted following the removal of native tissue, for example after tumor removal. In still other embodiments, a tissue treatment product is implanted following surgical separation of native tissues or in a wound or other void space that occurs through injury or disease. In some embodiments, implanting a tissue treatment product leads to faster healing, as compared to healing in the absence of an implanted tissue treatment product.

In various embodiments, method of treatment is provided, comprising the use of a tissue treatment product having a porous synthetic material and at least one chelating agent that is covalently bound to the porous material. In some embodiments, the tissue treatment product having a porous synthetic material is used to seal the surface of a wound or surgical incision, and the tissue treatment product provides a platform for the rapid attachment of metals and/or metal-binding proteins prior to surgical use in a subject. In some embodiments, the synthetic material is a polyurethane material. In certain embodiments, the tissue treatment product is functionalized with at least one metal and/or at least one metal binding protein. In some embodiments, using the tissue treatment product results in a wound site or surgical incision that has a lower level of bioburden, as compared to a wound site or surgical incision that is not contacted with a tissue treatment product.

DESCRIPTION OF CERTAIN EXEMPLARY EMBODIMENTS

Reference will now be made in detail to certain exemplary embodiments according to the present disclosure, certain examples of which are illustrated in the accompanying drawings.

In various embodiments, tissue treatment products are provided. In some embodiments, a tissue treatment product comprises the extracellular matrix of a partially or completely decellularized human or animal tissue. In other embodiments, a tissue treatment product comprises a synthetic material containing a structural scaffold into which native cells can migrate from tissue surrounding an implanted tissue treatment product and proliferate, thereby promoting tissue repair, regeneration, and/or treatment. In some embodiments, a tissue treatment product comprises at least one partially or completely decellularized human or animal tissue and at least one synthetic material containing a structural scaffold.

In certain embodiments, a tissue treatment product can be bound to at least one chelating agent. The chelating agents on the tissue treatment product can be used to sequester undesirable or harmful metals at the site of implantation. Alternatively, in certain embodiments the tissue treatment product can provide a flexible platform for the addition of a variety of additional functional reagents. For example, the one or more chelating agents on a tissue treatment product can be used to immobilize one or more metals, thereby yielding functionalized tissue treatment products. The metals can be chosen, in certain embodiments, for their antimicrobial properties, e.g., their ability to reduce or prevent the growth of microorganisms on a tissue treatment product after implantation into a recipient tissue. For example, the metal bound to the tissue treatment product can be silver, a metal that can inhibit the growth on an implanted tissue treatment product of microorganisms from the host environment. Furthermore, in some embodiments, immobilizing the antimicrobial metal on the tissue treatment product via a chelating agent reduces the amount of metal that will leach out of the tissue treatment product. Thus, in certain embodiments, a higher local concentration of antimicrobial metal can be achieved at the site of implantation while using a lower overall concentration.

In certain embodiments, the at least one metal bound to a tissue treatment product can be used to immobilize at least one metalloenzyme or other metal-binding protein on the product. The metal can be any metal (e.g., calcium, zinc, copper, cobalt, nickel, manganese, or magnesium) suitable for binding to a desired metalloenzyme or other metal-binding protein. The metalloenzyme or metal-binding protein can be chosen to provide any desired beneficial property after implantation into a tissue in need thereof. For example, the metalloenzyme can be lysostaphin, a peptidase that binds to zinc and can be used to reduce bioburden on a tissue treatment product. In another example, a tissue treatment product can be functionalized with one or more matrix metalloproteinases, which are important for regulation of cell proliferation, cell migration, cell differentiation, angiogenesis, and inflammation.

The tissue treatment products disclosed herein can be used, in various embodiments, to repair, regenerate, heal, treat, and/or alter a tissue in need thereof. For example, an implanted tissue treatment product can provide a biological or synthetic scaffold in which native cells from tissue surrounding an implanted tissue treatment product can migrate and proliferate. In addition, in certain embodiments the tissue treatment product can further have antimicrobial properties, thereby reducing or preventing an increase in the bioburden on a tissue treatment product after implantation into a host tissue. Similarly, in some embodiments the tissue treatment product can be used to deliver enzymes, signaling molecules, or other factors to the tissue in need of repair, regeneration, or treatment, thereby promoting or enhancing the repopulation and/or revascularization of the tissue treatment product with native cells from surrounding tissue.

The materials and methods provided herein can be used to make a biocompatible composition. As used herein, a "biocompatible" composition is one that has the ability to support the migration and proliferation of native cells from surrounding tissue into an implanted tissue treatment product. Biocompatible compositions support the native cellular activity necessary for tissue regeneration, repair, healing, or treatment and do not elicit a substantial immune response that prevents such cellular activity. As used herein, a "substantial immune response" is one that prevents partial or complete tissue regeneration, repair, healing, or treatment.

As used herein, the terms "native cells" and "native tissue" mean the cells or tissue present in the recipient organ or tissue prior to implantation of a tissue treatment product, or the cells or tissue produced by the host animal after implantation.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described here will be understood to include the endpoints and all values between the endpoints.

Tissue Treatment Products

In various embodiments, a tissue treatment product comprises human or animal tissue that has been at least partially decellularized. The tissue can be acellular, partially decellularized, and/or decellularized tissue that has been repopulated with exogenous cells, so long as the tissue retains at least some of the extracellular matrix found in the tissue prior to decellularizing.

In certain embodiments, the tissue treatment product can comprise a synthetic material having an artificial scaffold approximating the structure of the extracellular matrix from a human or animal tissue. For example, the tissue treatment product can comprise a scaffold derived from a hyaluronic acid derivative, chitosan, polycaprolactone, polyglycolide, polylactide, polydioxane (or other polyether esters), poly (lactide-co-glycolide), and/or polyhydroxyalkonate. In some embodiments, a tissue treatment product comprises a combination of at least one synthetic material and at least one animal or human tissue material, or it can comprise one or more synthetic materials alone, or one or more animal or human tissue materials alone. For example, the tissue treatment product can comprise a scaffold derived from hyaluronic acid and the acellular matrix of a decellularized tissue.

In some embodiments, a tissue treatment product can comprise an artificial material for use in wound repair or treatment. The product can provide a material to seal a wound while also serving as a platform for the delivery of various chelating agents, metals and/or metal-binding proteins, as described in further detail below. For example, the tissue treatment product for use in wound repair or treatment can comprise a polyurethane foam, such as V.A.C. GRANUFOAM (KCI, Inc., San Antonio, Tex.), alone or in combination with a partially or completely decellularized tissue.

In certain embodiments, a tissue treatment product can be derived from any human or animal tissue that is suitable for partial or complete decellularization and subsequent implantation. Exemplary tissues include, but are not limited to, bone, skin, dermis, intestine, urinary bladder, tendon, ligament, muscle, fascia, neurologic tissue, vessel, liver, heart, lung, kidney, cartilage, and/or any other suitable tissue. In certain embodiments, the tissue treatment product can include a mammalian soft tissue. For example, in certain embodiments, the tissue treatment product can include partially or completely decellularized mammalian dermis. In other embodiments, the tissue treatment product can comprise partially or completely decellularized small intestine submucosa, or partially or completely decellularized lung or liver tissue. In certain embodiments, the decellularized tissue can come from human or non-human sources. Exemplary, suitable non-human tissue sources include, but are not limited to, pigs, sheep, goats, rabbits, monkeys, and/or other non-human mammals.

In some embodiments, tissue treatment products can be formed from ALLODERM® or STRATTICE™ (Lifecell Corp., Branchburg, N.J.), which are human and porcine acellular dermal matrices respectively. Alternatively, any other suitable acellular tissue matrices can be used. For example, a number of biological scaffold materials are described by Badylak et al., and the methods of the present disclosure can be used to produce a stable three-dimensional acellular tissue matrix using any of those materials, or any other similar materials. Badylak et al., "Extracellular Matrix as a Biological Scaffold Material: Structure and Function," *Acta Biomaterialia* (2008), doi:10.1016/j.actbio.2008.09.013, hereby incorporated by reference in its entirety.

In various embodiments, the extracellular scaffold within an acellular or partially decellularized tissue matrix may consist of collagen, elastin, or other fibers, as well as proteoglycans, polysaccharides and growth factors. The tissue matrix may retain some or all the extracellular matrix components that are found naturally in a tissue prior to decellularization, or various undesirable components may be removed by chemical, enzymatic or genetic means. In general, the acellular matrix provides a structural network of fibers, proteoglycans, polysaccharides, and growth factors on which native tissue and vasculature can migrate, grow, and proliferate. The exact structural components of the extracellular matrix will depend on the tissue selected and the processes used to prepare the acellular or partially decellularized tissue.

In certain embodiments, a tissue treatment product lacks certain undesirable antigens. For example, certain animal tissues contain alpha-galactose ($\alpha$-gal) epitopes that are known to elicit reactions in humans. Therefore, acellular tissue treatment products derived from various animal tissues can be produced or processed to lack certain antigens, such as $\alpha$-gal. In some embodiments, tissue treatment products lack substantially all $\alpha$-gal moieties. Elimination of the $\alpha$-gal epitopes from a tissue treatment product may diminish the immune response against the composition. U. Galili et al., *J. Biol, Chem.* 263: 17755 (1988). Since non-primate mammals (e.g., pigs) produce $\alpha$-gal epitopes, xenotransplantation of acellular tissue matrix material from these mammals into primates may result in rejection because of primate anti-Gal binding to the $\alpha$-gal epitopes on the acellular tissue matrix. The binding results in the destruction of the acellular tissue by complement fixation and by antibody-dependent cell cytotoxicity. U. Galili et al., *Immunology Today* 14: 480 (1993); M. Sandrin et al., *Proc. Natl. Acad. Sci. USA* 90: 11391 (1993); H. Good et al., *Transplant. Proc.* 24: 559 (1992); B. H. Collins et al., *J. Immunol.* 154: 5500 (1995).

As described in detail below, in various embodiments, tissue treatment products can be processed to remove antigens such as $\alpha$-gal, e.g., by chemical or enzymatic treatment. Alternatively, tissue treatment products can be produced from animals that have been genetically modified to lack these epitopes.

Tissue treatment products can be selected to provide a variety of different biological and mechanical properties. For example, a tissue treatment product can be selected in order to provide a scaffold in which native cells from tissue surrounding an implanted tissue treatment product can migrate and proliferate, thereby enhancing the speed or overall level of repair, regeneration, healing, or treatment of native tissue. For example, an acellular tissue matrix, when implanted on or into fascia, may be selected to allow for regeneration of the fascia without excessive fibrosis or scar formation.

In certain embodiments, tissue treatment products comprising human or animal tissue are completely or substantially free of all cells normally present in the tissue from which the tissue treatment product is derived. As used herein, "substantially free of all cells" means that the tissue treatment product contains less than 20%, 10%, 5%, 1% 0.1%, 0.01%, 0.001%, or 0.0001% (or any percentage in between) of the cells that normally grow within the acellular matrix of the tissue prior to decellularization.

In some embodiments, tissue treatment products can include extracellular scaffolds that have been repopulated with viable cells. Various cell types can be used for repopulation, including stem cells such as embryonic stem cells, adult stem cells (e.g. mesenchymal stem cells), and/or neuronal cells. Any other viable cells can also be used. In some embodiments, the cells are mammalian cells. Such cells can promote native tissue migration, proliferation, and/or vascularization. In various embodiments, the viable cells are applied to the acellular tissue matrix before or after implantation of a tissue treatment product.

In certain embodiments, tissue treatment products comprise one or more additional agents. In some embodiments, the additional agent can comprise an anti-inflammatory agent, an analgesic, or any other desired therapeutic or beneficial agent. In certain embodiments, the additional agent can comprise, e.g., at least one added growth or signaling factor (e.g., a cell growth factor, an angiogenic factor, a differentiation factor, a cytokine, a hormone, and/or a chemokine). These additional agents can promote native tissue migration, proliferation, and/or vascularization. In some embodiments, the growth or signaling factor is encoded by a nucleic acid sequence contained within an expression vector. Preferably, the expression vector is in one or more of the viable cells that can be added, optionally, to a tissue treatment product. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, initiation and termination codons, etc.) to ensure at least minimal expression of the desired protein by the cell.

In various embodiments, a tissue treatment product bound to a chelating agent is provided. In certain embodiments, the tissue treatment product is coupled to at least one (e.g., 1, 2, 3, 4, 5, or more) chelating agents. The one or more chelating agents can comprise, in some embodiments, any chelating agent that can bind to a free amine, hydroxyl, or thiol group in the tissue treatment product. In certain embodiments, the chelating agent can comprise iminodiacetic acid (IDA), nitrilotriacetic acid (NTA), ethylenediaminetetraacetic acid (EDTA), and/or diethylenetriaminepentaacetic acid (DTPA). In certain embodiments, IDA is the chelating agent. In some embodiments, IDA is present on the tissue treatment product at a concentration of between about 0.025 mM and about 10.0 mM.

In some embodiments, the chelating agent is covalently bound to an activating agent that can covalently bind the tissue treatment product, e.g., by binding to free amine, hydroxyl, or thiol groups in the tissue treatment product. As used herein, an "activating agent" is any agent that can react with a chelating agent and enables the chelating agent to covalently bind to a tissue treatment product. For example, an activating agent can react with a carboxylic acid group in a chelating agent to form an ester that will react with an amine group on a tissue treatment product. In certain embodiments, the activating agent is N-hydroxysulfosuccinimide (NHS), suberic acid bis(N-hydroxysuccinimide ester), 1,4-butanediol diglycidyl ether, epibromohydrin, or 1,2,7,8-diepoxyoctane.

In various embodiments, the tissue treatment product bound to at least one chelating agent can serve as a platform for the attachment of a number of different metals, proteins, and/or other chemical additives. For example, any desired metal, protein, and/or other chemical that is capable of binding a chelating agent can be easily attached to the tissue treatment product by contacting the tissue with the metal, protein, and/or other chemical agent. Similarly, any metal-binding protein can be easily attached to the tissue treatment product by contacting the tissue with the appropriate metal and the desired protein.

Accordingly, in certain embodiments, a tissue treatment product bound to at least one chelating agent, as disclosed herein, provides a flexible platform for the co-delivery of the tissue treatment product and a wide variety of additional components or additives to a site of tissue treatment, repair, and/or regeneration. The additional components can be interchanged by contacting the tissue treatment product that is bound to at least one chelating agent with a different additional component. Furthermore, because the additional components are immobilized on the tissue treatment product via binding to the chelating agent, they will not migrate, dissolve, or disperse from the site of implantation. Thus, a higher local concentration of the additives can be maintained while using a lower overall concentration of additives.

In addition to the flexible platform provided by tissue treatment products bound to chelating agents, in certain embodiments the one or more chelating agents on a tissue treatment product can directly provide certain beneficial properties following implantation of the tissue treatment product into a host site. For example, the chelating agent bound to the acellular tissue or synthetic material (e.g., polyurethane foam, hyaluronic acid derivative, chitosan, polycaprolactone, polyglycolide, polylactide, polydioxane (or other polyether esters), poly(lactide-co-glycolide), and/or polyhydroxyalkonates) can serve to sequester or remove undesirable metals from a site of implantation.

In certain embodiments, a functionalized tissue treatment product is provided, comprising a tissue treatment product bound to a chelating agent and at least one metal (e.g., at least 1, 2, 3, 4, 5, or more metals). The chelating agent on the tissue treatment product serves to bind and immobilize the metal on the tissue treatment product. In some embodiments, IDA, NTA, EDTA, DTPA is the chelating agent that immobilizes the metal. In certain embodiments, IDA is the chelating agent that immobilizes the at least one metal on the tissue treatment product. In some embodiments, the metal is calcium, zinc, copper, magnesium, manganese, cobalt, nickel and/or silver. In some embodiments, calcium, zinc, copper, cobalt, nickel, magnesium, manganese, and/or silver is immobilized by IDA, NTA, EDTA, and/or DTPA on the tissue treatment product. In some embodiments, zinc is immobilized by IDA on the tissue treatment product.

In various embodiments, the metal that is immobilized on the tissue treatment product is selected for its antimicrobial properties or its ability to inhibit the growth of bacteria on a tissue treatment product. For example, the metals such as silver, zinc, and copper are known to inhibit the growth of bacteria. These metals can be used, e.g., to prevent bacteria at a site of implantation from growing on an implanted tissue treatment product. Any other metal with similar properties can also be used. In certain embodiments, a combination of at least two different metals (e.g., 2, 3, 4, 5, or more) having antimicrobial or bacterial growth inhibitory properties are used. The metal or metals are immobilized on the tissue treatment product through interaction with the chelating agent, thereby preventing the metal from diffusing into the aqueous environment of the implant site. In certain embodiments, the concentration of metal on the tissue treatment product is sufficient to reduce bioburden. In some embodiments, a sufficient concentration of metal is achieved by contacting the tissue treatment product with a solution containing the metal at a concentration of at least about 0.5, 1.0, 1.5, 2.0 mM (or any concentration in between).

In various embodiments, the metal that is immobilized on the tissue treatment product is selected for its ability to serve as a binding site for one or more (e.g., 1, 2, 3, 4, 5, or more) desired metalloenzymes or metal-binding proteins. For example, many metalloenzymes or metal-binding proteins will bind to calcium, magnesium, manganese, zinc, cobalt, nickel, and/or copper. Accordingly, in certain embodiments, the immobilized metal is calcium, magnesium, manganese, zinc, cobalt, nickel, and/or copper, thereby providing one or more binding sites for one or more metalloenzymes or metal-binding proteins.

In various embodiments, a functionalized tissue treatment product is provided, comprising a tissue treatment product bound to a chelating agent and at least one metal, and further comprising a metalloenzyme or metal-binding protein. In various embodiments, the metalloenzyme or metal-binding protein is any desired bioactive compound capable of binding to a metal that is immobilized on a tissue treatment product. In some embodiments, one or more such bioactive compounds (e.g., 1, 2, 3, 4, 5, or more bioactive compounds) are bound to the tissue treatment product. In some embodiments, the metalloenzymes or metal-binding proteins are capable of binding to a metal (e.g., magnesium, manganese, calcium, zinc, cobalt, nickel, and/or copper) that is immobilized on a tissue treatment product.

In various embodiments, the one or more metalloenzymes or metal-binding proteins are selected from antimicrobial metallopeptidases or matrix metalloproteinases. In certain embodiments, the metallopeptidase or matrix metalloproteinase retains its antimicrobial properties (e.g., the ability to reduce or inhibit bioburden on the tissue treatment product) after binding to metal on the tissue treatment product. In one embodiment, the antimicrobial metallopeptidase used is lysostaphin. Lysostaphin is a zinc binding peptidase that can cleave the cell walls of certain species of staphylococci, such as *S. aureus*, resulting in bacterial cell death. Thus, in certain embodiments, the functionalized tissue treatment product comprises lysostaphin bound to zinc immobilized on a tissue treatment product. In some embodiments, use of tissue treatment products functionalized with lysostaphin can help reduce bioburden on an implanted tissue treatment product, and thereby promote or enhance tissue treatment, repair, and/or regeneration (e.g., by reducing the risk of infection at the site of implantation).

In some embodiments, the functionalized tissue treatment product comprises at least one matrix metalloproteinase. Matrix metalloproteinases are a family of proteolytic enzymes involved in the remodeling of extracellular matrices. The enzymes act by cleaving specific regions having extracellular matrix proteins and provide a means for promoting cell migration into and regeneration of implanted tissue treatment products. Matrix metalloproteinases are important for regulation of cell proliferation, migration, differentiation, angiogenesis, and inflammation. Thus, in some embodiments, the use of tissue treatment products functionalized with matrix metalloproteinases can promote or enhance tissue treatment, repair, and/or regeneration.

In various embodiments, tissue treatment products are functionalized with metal and/or metalloenzymes and/or metal-binding proteins that are selected for their ability to reduced or inhibit bioburden (i.e., their ability to reduce the number of microorganisms growing on the compositions, or to prevent an increase in the number of microorganisms that can grow on the compositions). Thus, in some embodiments, the functionalized tissue treatment products have reduced bioburden or do not exhibit an increase in bioburden following implantation into a host tissue. In some embodiments, a functionalized tissue treatment product lacks substantially all bioburden (i.e., the tissue treatment products are aseptic or sterile). As used herein, "lacking substantially all bioburden" means a tissue treatment product in which the concentration of growing microorganisms is less than 1%, 0.1%, 0.01%, 0.001%, or 0.0001% (or any percentage in between) of that growing on tissue treatment products that have not been functionalized.

Tissue treatment products, as described above, may be provided packaged, frozen, freeze-dried, hydrated, and/or dehydrated. In certain embodiments, the packaged tissue treatment products are sterile. In certain embodiments, the tissue treatment products are provided in a kit, comprising a packaged tissue treatment product and instructions for preparing and/or using the tissue treatment products.

Methods of Making Tissue Treatment Products

Disclosed herein are methods of making tissue treatment products. In some embodiments, the method comprises selecting a tissue containing an extracellular collagen matrix; partially or completely decellularizing the tissue; binding at least one chelating agent to the tissue; and functionalizing the tissue with at least one metal, metalloenzyme, and/or metal-binding protein. In some embodiments, a synthetic material, such as a hyaluronic acid derivative, chitosan, polycaprolactone, polyglycolide, polylactide, polydioxane (or other polyether esters), poly(lactide-co-glycolide), and/or polyhydroxyalkonates, is used alone or in combination with a decellularized tissue to provide an artificial scaffold for the migration and proliferation of native cells from tissue surrounding an implant site. In such embodiments, the method of making a tissue treatment product comprises selecting synthetic material; optionally selecting a tissue containing an extracellular collagen matrix and partially or completely decellularizing the tissue; optionally combining the synthetic material with the partially or completely decellularized tissue; binding at least one chelating agent to the synthetic material and/or to the partially or completely decellularized tissue; and functionalizing by contacting the tissue treatment product with at least metal, metalloenzyme, and/or metal-binding protein.

In other embodiments, a synthetic material, such as a polyurethane foam (e.g., GRANUFOAM®, Kinetics Concepts, Inc., San Antonio, Tex.), can be used alone, or in combination with a decellularized tissue, as a wound treatment or repair product. In these embodiments, the tissue treatment product serves to seal a wound while providing a platform for the delivery of a variety of chelating agents, metals, and/or metal-binding proteins to a wound site. In some embodiments, where synthetic materials are used, the method comprises selecting a synthetic material, binding at least one chelating agent to the material; and functionalizing the material with at least one metal, metalloenzyme, and/or metal-binding protein.

In some embodiments, a tissue treatment product can be prepared from any tissue that is suitable for decellularization and subsequent implantation. Exemplary tissues include, but are not limited to, bone, skin, dermis, intestine, urinary bladder, tendon, ligament, muscle, fascia, neurologic tissue, vascular tissue, vessel, liver, heart, lung, kidney, cartilage, and/or any other suitable tissue. In certain embodiments, the tissues can include a mammalian soft tissue. For example, in certain embodiments, the tissue can comprise mammalian dermis. In certain embodiments, the dermis can be separated from surrounding epidermis and/or other tissues, such as subcutaneous fat. In certain embodiments, the tissue can comprise small intestine submucosa. In certain embodiments, the tissue can include human or non-human sources. Exemplary, suitable non-human tissue sources include, but are not limited to, pigs, sheep, goats, cow, rabbits, monkeys, and/or other non-human mammals.

In some embodiments, a tissue treatment product is prepared by partially or completely decellularizing a donor tissue. Exemplary methods for decellularizing tissue are disclosed in U.S. Pat. No. 6,933,326 and U.S. Patent Application 2010/0272782, which are hereby incorporated by reference in their entirety. In some embodiments, the decellularized tissue provides a porous extracellular scaffold structure into which cells from surrounding native tissue can migrate and proliferate after implantation into a host site. In certain exemplary embodiments, the acellular tissue comprises ALLODERM® or STRATTICE™, which are acellular human dermal products and porcine dermal products, respectively, and are available from LifeCell Corporation (Branchburg, N.J.).

In various embodiments, the general steps involved in the production of an acellular or partially decellularized tissue matrix include providing tissue from a donor (e.g., a human cadaver or animal source) and removing cells under conditions that preserve the biological and structural function of the extracellular matrix. In certain embodiments, the tissue can be washed to remove any residual cryoprotectants and/or other contaminants. Solutions used for washing can be any physiologically compatible solution. Examples of suitable wash solutions include distilled water, phosphate buffered saline (PBS), or any other biocompatible saline solution.

In certain embodiments, the washed tissue can be chemically treated to stabilize the tissue so as to avoid biochemical and/or structural degradation before, during, or after cell removal. In various embodiments, the stabilizing solution arrests and prevents osmotic, hypoxic, autolytic, and/or proteolytic degradation; protects against microbial contamination; and/or reduces mechanical damage that can occur during decellularization of tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

In various embodiments, the tissue is then placed in a decellularization solution to remove viable and non-viable cells (e.g., epithelial cells, endothelial cells, smooth muscle cells, and fibroblasts, etc.) from the extracellular matrix without damaging the biological and/or structural integrity of the extracellular matrix. The decellularization solution may contain an appropriate buffer, salt, an antibiotic, one or more detergents (e.g., TRITON X-100™, sodium dodecyl sulfate, sodium deoxycholate, polyoxyethylene (20) sorbitan mono-oleate, etc.), one or more agents to prevent cross-linking, one or more protease inhibitors, and/or one or more enzymes. In some embodiments, the decellularization solution comprises 0.1%, 0.2%, 0.3%, 0.4%, 0.5%, 1.0%, 1.5%, 2.0%, 2.5%, 3.0%, 3.5%, 4.0%, 4.5%, or 5.0% (or any percentage in between) of TRITON X-100™ and, optionally, 10 mM, 15 mM, 20 mM, 25 mM, 30 mM, 35 mM, 40 mM, 45 mM, or 50 mM EDTA (ethylenediaminetetraacetic acid) (or any concentration in between). In some embodiments, the tissue is incubated in the decellularization solution at 25, 30, 31, 32, 33, 34, 35, 36, 37, 38, 39, 40, 41, or 42 degrees Celsius (or any temperature in between), and optionally, gentle shaking is applied at 10, 20, 30, 40, 50, 60, 70, 80, 90, 100, 110, 120, 130, 140, or 150 rpm (or any rpm in between). The incubation can be for 1, 2, 3, 4, 5, 6, 7, 8, 9, 10, 11, 12, 15, 20, 24, 36, or 48 hours (or any time in between). The length of time of exposure to the decellularization solution, or the concentration of detergent and/or other decellularizing agents can be adjusted in order to partially or more fully decellularize the tissue. In certain embodiments, additional detergents may be used to remove cells from the tissue sample. For example, in some embodiments, 1, 2, 3, 4, or 5% (or any percentage in between) sodium deoxycholate (or any percentage in between) is added to the decellularization solution in order to remove fat cells from the tissue.

In some embodiments, after decellularization, the tissue sample is washed thoroughly. Any physiologically-compatible solutions can be used for washing. Examples of suitable wash solutions include distilled water, phosphate buffered saline (PBS), or any other biocompatible saline solution. In certain embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable DNase buffer can be used, as long as the buffer provides for suitable DNase activity.

While an acellular or partially decellularized tissue matrix may be derived from tissue from one or more donor animals of the same species as the intended recipient animal, this is not necessarily the case. Thus, for example, an acellular tissue matrix may be derived from porcine tissue and implanted in a human patient. Species that can serve as donors and/or recipients of acellular tissue matrices include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

In certain embodiments, decellularized tissue can be treated with one or more enzymes to remove undesirable antigens, e.g., an antigen not normally expressed by the recipient animal and thus likely to lead to an immune response and/or rejection of the implanted tissue treatment product. For example, in certain embodiments, decellularized tissue can be treated with alpha-galactosidase to remove alpha-galactose (α-gal) moieties. In some embodiments, to enzymatically remove α-gal epitopes, after washing tissue thoroughly with saline, the tissue may be subjected to one or more enzymatic treatments to remove α-gal antigens, if present in the sample. In certain embodiments, the tissue may be treated with an α-galactosidase enzyme to eliminate α-gal epitopes. In one embodiment, the tissue is treated with α-galactosidase at a concentration of 0.2 U/ml prepared in 100 mM phosphate buffered saline at pH 6.0. In other embodiments, the concentration of α-galactosidase is reduced to 0.1 U/ml or reared to 0.3, 0.4, or 0.5 U/ml (or any value in between). In other embodiments, any suitable enzyme concentration and buffer can be used, as long as sufficient antigen removal is achieved. In addition, certain exemplary methods of processing tissues to reduce or remove alpha-1,3-galactose moieties are described in Xu et al., *Tissue Engineering*, Vol. 15, 1-13 (2009), which is hereby incorporated by reference in its entirety.

In certain embodiments, animals that have been genetically modified to lack one or more antigenic epitopes may be selected as the tissue source for a tissue treatment product. For example, animals (e.g., pigs) that have been genetically engineered to lack the terminal α-galactose moiety can be selected as the tissue source. For descriptions of appropriate animals and methods of producing transgenic animals for xenotransplantation, see U.S. patent application Ser. No. 10/896,594 and U.S. Pat. No. 6,166,288, which are hereby incorporated by reference in their entirety.

In some embodiments, the decellularized tissue can be treated to reduce bioburden (i.e., to reduce the number of microorganisms growing on the tissue). In some embodiments, the tissue is treated such that it lacks substantially all bioburden (i.e., the tissue is aseptic or sterile). Suitable bioburden reduction methods are known to one of skill in the art, and may include exposing the tissue treatment product to radiation. Irradiation may reduce or substantially eliminate bioburden. In some embodiments, an absorbed dose of 15-17 kGy of e-beam radiation is delivered in order to reduce or substantially eliminate bioburden. In various embodiments, the amount of radiation to which the tissue treatment product is exposed can be between 5 Gy and 50 kGy. Suitable forms of radiation can include gamma radiation, e-beam radiation, and X-ray radiation. Other irradiation methods are described in U.S. Application 2010/0272782, the disclosure of which is hereby incorporated by reference in its entirety.

In various embodiments, a synthetic material can be used in place of or in combination with an acellular tissue to provide an extracellular scaffold in a tissue treatment product. For example, a tissue treatment product can comprise a synthetic material such as a hyaluronic acid derivative, chitosan, polycaprolactone, polyglycolide, polylactide, polydioxane (or other polyether esters), poly(lactide-co-glycolide), and/or polyhydroxyalkonates in place of acellular tissue. In some embodiments, a tissue treatment product comprises a combination of natural and synthetic matrix scaffold components (e.g., a combination of hyaluronic acid derivatives and acellular or partially decellularized tissue).

In certain embodiments, after the natural or artificial scaffold of a tissue treatment product is formed, viable cells may optionally be seeded in the matrix. In some embodiments, viable cells may be added to the matrices by standard in vitro cell co-culturing techniques prior to transplantation, or by in vivo repopulation following transplantation. In vivo repopulation can be by the migration of native cells from surrounding tissue into the matrix or by infusing or injecting viable cells obtained from the recipient or from another donor into the matrix in situ. Various cell types can be used, including stem cells such as embryonic stem cells and/or adult stem cells (e.g. mesenchymal stem cells). Any other viable cells can also be used. In some embodiments, the cells are mammalian cells. In certain embodiments, the cells are histocompatible with the subject in which they are implanted. Such cells can promote native tissue migration, proliferation, and/or vascularization. In various embodiments, the cells can be directly applied to the matrix of a tissue treatment product just before or after implantation.

In certain embodiments, one or more additional agents can be added to the extracellular matrix of a tissue treatment product. In some embodiments, the additional agent can comprise an anti-inflammatory agent, an analgesic, or any other desired therapeutic or beneficial agent. In certain embodiments, the additional agent can comprise at least one added growth or signaling factor (e.g., a cell growth factor, an angiogenic factor, a differentiation factor, a cytokine, a hormone, and/or a chemokine). In some embodiments, these additional agents can promote native tissue migration, proliferation, and/or vascularization within the implanted tissue product. In some embodiments, the growth or signaling factor is encoded by a nucleic acid sequence contained within an expression vector. Preferably, the expression vector is in one or more of the viable cells that can be included, optionally, in a tissue treatment product. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, termination codon, etc.) to ensure at least minimal expression of the desired protein by the cell.

In various embodiments, a tissue treatment product (comprising a partially or fully decellularized tissue or a synthetic material that provides an extracellular scaffold) is bound to at least one (e.g., 1, 2, 3, 4, 5, or more) chelating agents. The one or more chelating agents can comprise, in some embodiments, any chelating agent that can bind to a free amine, hydroxyl, and/or thiol group in the tissue treatment product. In certain embodiments, the chelating agent can comprise IDA, NTA, EDTA, and/or DTPA. In certain embodiments, IDA is the chelating agent. In some embodiments, IDA is used at a concentration of between about 0.025 mM and about 10.0 mM.

Figure 1A:
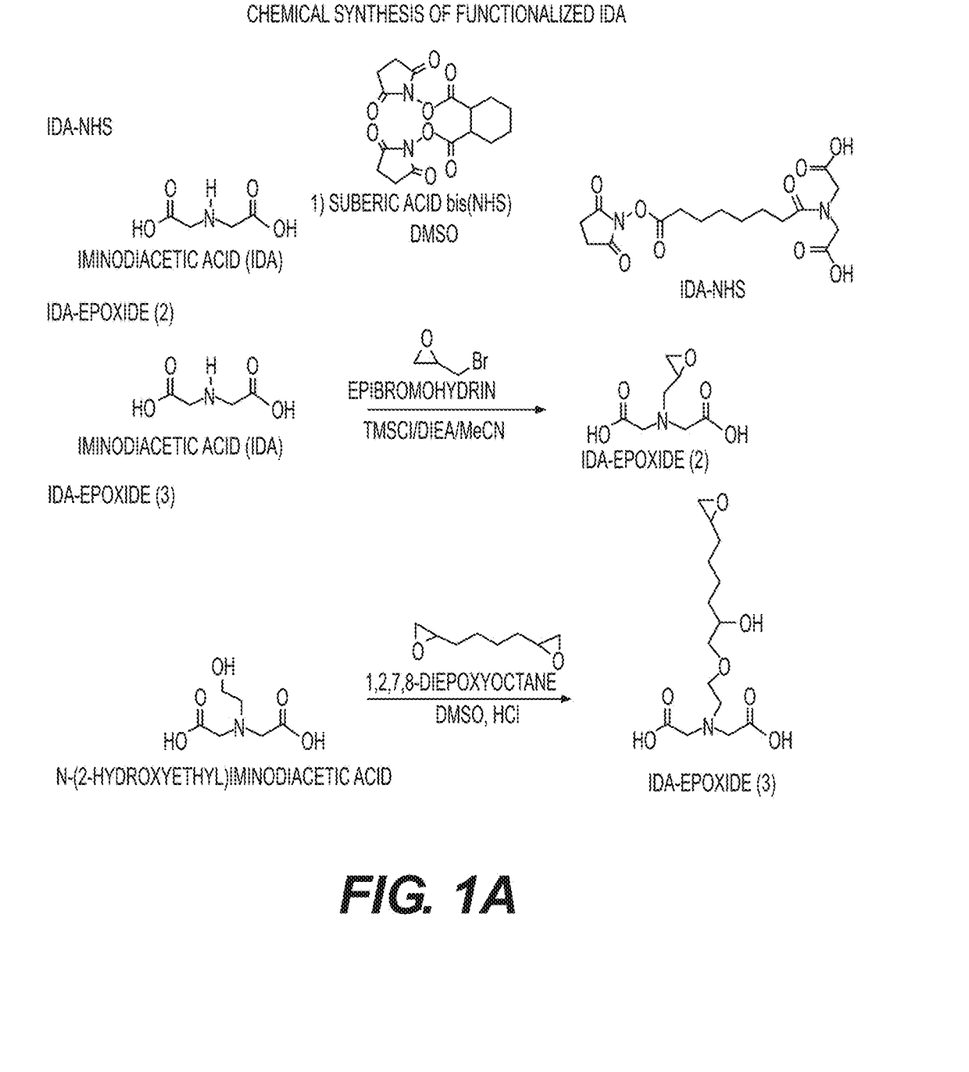
FIG. 1A shows methods, according to certain embodiments of the present disclosure, of preparing activated iminodiacetic acid (IDA) by reacting IDA with N-hydroxysulfosuccinimide (NHS) to form an IDA-NHS derivative, or by reacting IDA with epibromohydrin or 1,2,7,8-diepoxyoctane to form IDA-epoxide derivatives. In the figure, DMSO refers to dimethyl sulfoxide, TMSCl refers to trimethylsilyl chloride, DIEA refers to N,N-Diisopropylethylamine, MeCN refers to acetonitrile, and HCl is hydrogen chloride.

In certain embodiments, a chelating agent, such as IDA, NTA, EDTA, and/or DTPA, is first reacted with an activating agent. The activated chelating agent is then covalently bound to the tissue treatment product, e.g., by binding to free amine, hydroxyl, or thiol groups in the tissue treatment product. In some embodiments, the activating agent is N-hydroxysulfosuccinimide (NHS). NHS can serve to covalently bind the chelating agent to free amines present in the tissue treatment product, thereby immobilizing the chelating agent on the product. In alternative embodiments, the activating agent is epibromohydrin or 1,2,7,8-diepoxyoctane. The epoxide-derivatives of chelating agents produced by these activating agents can then covalently bind to free amine, thiol, or hydroxyl groups on the tissue treatment product, thereby immobilizing the chelating agent on the product. FIG. 1A illustrates exemplary methods of activating IDA using NHS, epibromohydrin, and 1,2,7,8-diepoxyoctane.

In certain embodiments where the tissue treatment product comprises an extracellular scaffold provided by a synthetic material, the tissue treatment product can be bound to one or more chelating agents during the manufacture of the synthetic material. In other embodiments, the tissue treatment product can be bound to one or more chelating agents subsequent to the manufacture of the synthetic material. For example, binding can be done immediately prior to implantation of the tissue treatment product.

In various embodiments, a tissue treatment product bound to one or more chelating agents can serve as a platform for the attachment of a number of different metals, proteins, and/or other chemical additives. For example, any desired metal, protein and/or other chemical that is capable of being immobilized by a chelating agent can be easily attached to the tissue treatment product by contacting the product with the metal, protein, and/or other chemical agent. Similarly, any metal-binding protein can be easily attached to the tissue treatment product by contacting the product with the appropriate metal and the desired protein.

In certain embodiments, a tissue treatment product that is bound to one or more chelating agents is functionalized by contacting the product with a solution containing at least one (e.g., 1, 2, 3, 4, 5, or more) metal. The metal will interact with the chelating agent on the tissue treatment product, thereby immobilizing the metal on the product. Suitable metals for use in functionalized tissue treatment products include any metal capable of interacting with a chelating agent on a tissue treatment product and having desirable properties.

In some embodiments, metals that provide antimicrobial properties (e.g., silver, zinc, and/or copper) can be used. As used herein, a metal having antimicrobial properties is one that reduces or inhibits bioburden (i.e., results in a reduced number of microorganisms growing on the tissue treatment product or prevents an increase in the number of microorganisms growing on the tissue treatment product after implantation into a host tissue), as compared to the tissue treatment product in the absence of metal functionalization. In some embodiments, a tissue treatment product is functionalized with at least one metal such that the resulting tissue product lacks substantially all bioburden (i.e., the tissue treatment product is aseptic or sterile). As used herein, "lacking substantially all bioburden" means a tissue treatment product in which the concentration of growing microorganisms is less than 1%, 0.1%, 0.01%, 0.001%, or 0.0001% (or any percentage in between) of that growing on untreated tissue treatment products.

In some embodiments, a tissue treatment product having antimicrobial properties is prepared by contacting the tissue treatment product with a solution containing a high enough concentration of metal such that the metal that binds to the functionalized tissue treatment product will be sufficient to produce a reduced bioburden. In certain embodiments, a sufficient concentration of metal is achieved by contacting the tissue treatment product with a solution containing the metal at a concentration of at least about 0.5, 1.0, 1.5, 2.0 mM (or any concentration in between). In some embodiments, the metal is zinc and is present in solution at a concentration of at least about 0.5, 1.0, 1.5, 2.0 mM (or any concentration in between).

In some embodiments, a tissue treatment product bound to one or more chelating agents is functionalized by contacting it with a solution containing calcium, zinc, magnesium, manganese, cobalt, nickel, silver, and/or copper. In some embodiments, calcium, zinc, magnesium, manganese, cobalt, nickel, silver, and/or copper in the solution is at a concentration of about 1.0 to about 10 mM (e.g., about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 mM, or any concentration in between).

In some embodiments, the chelating agent IDA is bound to a tissue treatment product, which is then functionalized with silver, zinc, and/or copper. In certain embodiments, tissue treatment products functionalized with silver, zinc, and/or copper have reduced bioburden or do not exhibit an increase in bioburden after implantation into a host tissue, as compared to implanted tissue treatment products that were not functionalized with metal. In some embodiments, tissue treatment products functionalized with silver, zinc, and/or copper lack substantially all bioburden.

In various embodiments, a tissue treatment product that has been functionalized with at least one metal is further functionalized by contacting the tissue treatment product with a solution containing at least one (e.g., 1, 2, 3, 4, 5, or more) metalloenzymes or other metal-binding proteins that have desired properties. The one or more metalloenzymes or other metal-binding proteins are chosen for their ability to bind metal ions (e.g., calcium, zinc, magnesium, manganese, cobalt, nickel, and/or copper) that are immobilized on a tissue treatment product. In certain embodiments, the metal (which is bound to the tissue treatment product via the chelating agent) serves to immobilize the metalloenzyme or other metal-binding protein on the tissue treatment product.

Figure 1B:
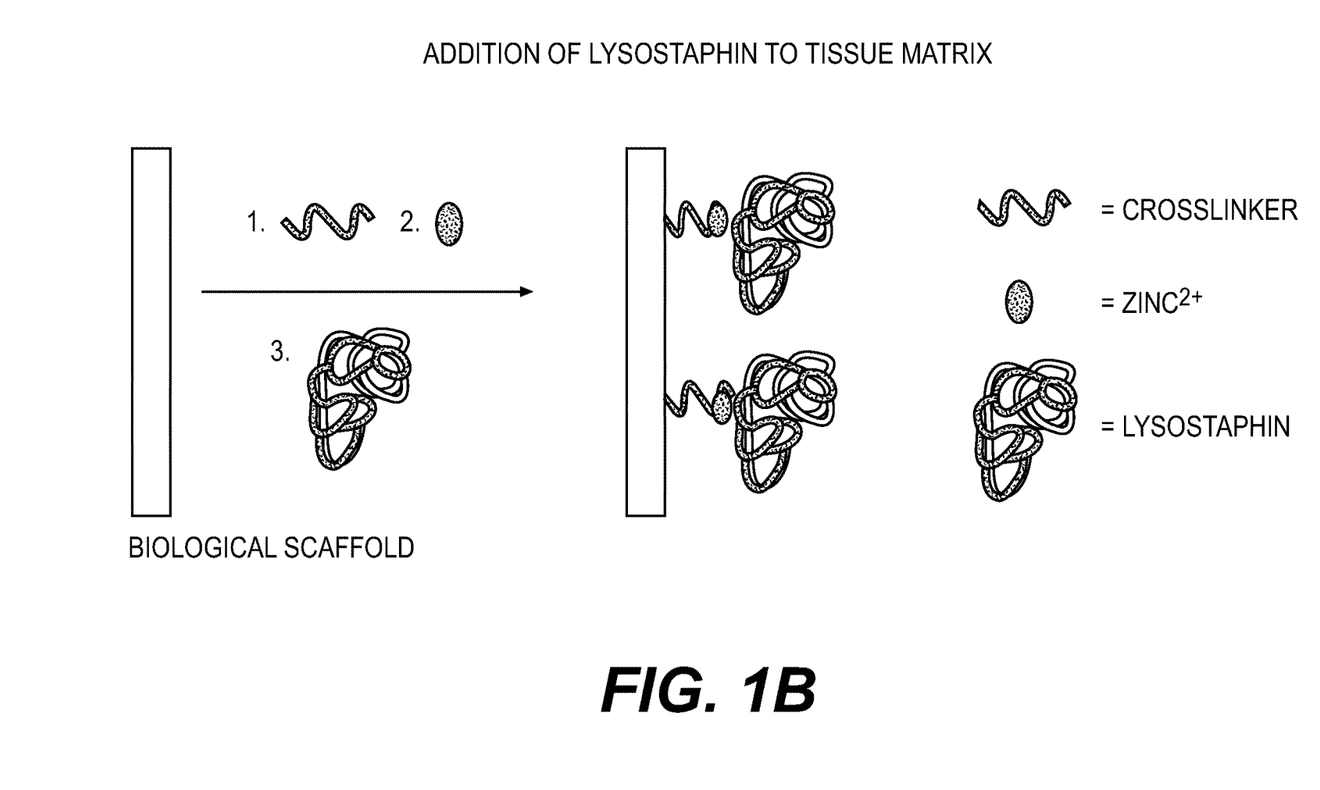
FIG. 1B shows a method, according to certain embodiments, of functionalizing a tissue treatment product by binding zinc and lysostaphin to a chelating agent on a tissue treatment product. The vertical bar in the figure represents the tissue treatment product, while the objects marked as "1" "2" and "3" represent a crosslinker, $Zn^{2+}$, and lysostaphin.

In various embodiments, the one or more metalloenzymes or metal-binding proteins are selected from antimicrobial metallopeptidases or matrix metalloproteinases. In certain embodiments, after binding to the metal on the tissue treatment product, the metallopeptidase or matrix metalloproteinase retains its antimicrobial properties (e.g., the ability to reduce bioburden on the tissue product or to prevent an increase in bioburden after implantation into a host tissue). In one embodiment, the antimicrobial metallopeptidase used is lysostaphin. In certain embodiments, a zinc-functionalized tissue treatment product is further functionalized by contacting it with a solution containing lysostaphin, which binds to zinc on the tissue treatment product. In some embodiments, functionalizing with lysostaphin comprises contacting the tissue treatment product with a lysostaphin solution at a concentration of about 1.0 to about 1000 µg/ml (e.g., about 1.0, 1.5, 2.0, 2.5, 3.0, 4.0, 5.0, 10.0, 20.0, 50.0, 100, 200, 500, or 1000 µg/ml, or any concentration in between). FIG. 1B illustrates one exemplary method for functionalizing a tissue treatment product with lysostaphin.

In certain embodiments, a tissue treatment product is bound to IDA, functionalized with zinc, and further functionalized with lysostaphin. In some embodiments, functionalizing with lysostaphin comprises contacting the tissue treatment product with a lysostaphin solution at a concentration of about 1.0 to about 1000 µg/ml (e.g., about 1.0, 1.5, 2.0, 2.5, 3.0, 4.0, 5.0, 10.0, 20.0, 50.0, 100, 200, 500, or 1000 µg/ml, or any concentration in between). In some embodiments, the use of tissue treatment products functionalized with lysostaphin can help reduce bioburden on an implanted tissue treatment product, and thereby promote or enhance tissue treatment, repair, and/or regeneration (e.g., by reducing the risk of infection at the site of implantation or by leading to the early failure or disintegration of the implant).

In some embodiments, a tissue treatment product functionalized with metal is further functionalized by contacting it with a solution containing at least one (e.g., 1, 2, 3, 4, 5, or more) matrix metalloproteinase. Matrix metalloproteinases are important for regulation of cell proliferation, migration, differentiation, angiogenesis, and inflammation. In some embodiments, the one or more matrix metalloproteinase comprises collagenase, gelatinase, stromolysin, matrilysin, and/or elastase. Thus, in some embodiments, functionalization with matrix metalloproteinases can promote or enhance tissue treatment, repair, and/or regeneration.

In various embodiments, the metal, metalloenzymes and/or metal-binding proteins that are used to functionalize tissue treatment products are selected for their ability to reduced or inhibit bioburden (i.e., to reduce the number of microorganisms or to prevent an increase in the number of microorganisms growing on an implanted tissue treatment product). In some embodiments, a functionalized tissue treatment product lacks substantially all bioburden.

Methods of Use

Disclosed herein are methods of using the tissue treatment products described above. In various embodiments, the tissue treatment products are implanted into a host tissue in need of repair, regeneration, or treatment. The extracellular matrix provided by the decellularized tissue or by the synthetic material (e.g., chitosan, polycaprolactone, polyglycolide, polylactide, polydioxane (or other polyether esters), poly(lactide-co-glycolide), and/or polyhydroxyalkonates) in the tissue treatment product can provide a scaffold into which native cells from surrounding tissue can migrate and proliferate. Accordingly, in certain embodiments, the scaffolds provided by tissue treatment products can enhance and/or promote tissue treatment, repair, and/or regeneration. Furthermore, as discussed in more detail below, the tissue treatment products can be used, in certain embodiments, to deliver additional compounds having various desirable properties, such as antimicrobial agents and/or compounds that enhance native cell migration, proliferation, and revascularization within the implanted tissue treatment product.

In some embodiments, a tissue treatment product can be used in wound repair or treatment. The product can provide a material to seal a wound while also serving as a platform for the delivery of various chelating agents, metals and/or metal-binding proteins, as described in further detail below. For example, the tissue treatment product for use in wound repair or treatment can comprise a polyurethane foam, such as V.A.C. GRANUFOAM® (Kinetics Concepts, Inc., San Antonio, Tex.), alone or in combination with a partially or completely decellularized tissue.

In certain embodiments, tissue treatment products that have been bound to at least one chelating agent can be implanted into a host tissue and used to sequester undesirable metals while also providing an extracellular scaffold that promotes native cell migration and proliferation. For example, tissue treatment products that have been bound to IDA can be used to sequester or remove zinc from an implant site, such as a wound site containing with zinc. In certain circumstances, it may be desirable to reduce zinc levels at an implant site, for example in order to increase hemoglobin levels, e.g., following surgery. See O'Neil-Cutting et al., *J. Nutr.* 111: 1969-79 (1981) (showing that elevated levels of zinc can lower hemoglobin levels). In other examples, any harmful or undesirable metal can be sequestered by binding to one or more chelating agents bound to a tissue treatment product.

In certain embodiments, a tissue treatment product bound to one or more chelating agents can serve as a flexible platform for the quick and easy delivery of a wide variety of metals and/or metal-binding proteins. For example, a tissue treatment product bound to one or more chelating agents can be provided, e.g., to a surgical facility, and quickly coupled at the facility to a wide variety of metals or metal-binding proteins by contacting the tissue treatment product with one or more metals and, optionally, one or more metal-binding proteins prior to implantation. In some embodiments, a kit is provided, comprising a sterile tissue treatment product bound to one or more chelating agents, a selection of sterile solutions comprising one or more metals, and/or a selection of sterile solutions comprising one or more metal-binding proteins. The surgical facility can then, in certain embodiments, prepare the desired functionalized tissue treatment product by contacting the tissue treatment product bound to one or more chelating agents with the desired metals and/or metal-binding proteins prior to surgical use. In this way, a surgical facility can quickly prepare a wide variety of different functionalized products without needing to order each functionalized product individually from a tissue supplier.

In certain embodiments, a tissue treatment product that has been functionalized with one or more metals is implanted in a patient. In some embodiments, the tissue treatment product that is implanted in a patient is functionalized with one or more metals that are selected for their antimicrobial properties (i.e., their ability to reduce or prevent an increase in the bioburden on the tissue treatment product after implantation). Effective concentrations of the antimicrobial metal will vary depending on the type of metal used and the desired reduction in bioburden. Methods of determining effective concentration are known to one of skill in the art and include, e.g., measuring differences in bioburden following implantation of tissue treatment products containing different concentrations of metal, or deliberate bacterial infection at the site of implantation and subsequent measurement of bioburden on implanted tissue treatment products containing different concentrations of metal. For example, the antimicrobial metal bound to the tissue treatment product can be silver. In some embodiments, the silver In certain embodiments, the implanted tissue treatment product that is functionalized with an antimicrobial metal has, at any point in time following implantation into a host tissue, at least a 5, 10, 15, 20, 25, 30, 35, 40, 45, 50, 55, 60, 65, 70, 75, 80, 85, 90, 95, 96, 97, 98, or 99% (or any percentage in between) lower concentration of microorganisms growing on the product, as compared to implanted tissue treatment product that is not functionalized with an antimicrobial metal. Furthermore, by immobilizing the antimicrobial metal to the tissue treatment product via a chelating agent, the functionalized tissue treatment product reduces, in some embodiments, the amount of metal that will leach out of the product. Thus, in certain embodiments, a higher local concentration of antimicrobial metal can be achieved at the site of implantation while using a lower overall concentration. In other embodiments, the harmful effects associated with certain antimicrobial metals can be reduced or prevented by immobilizing the metal on a tissue treatment product while retaining the beneficial reduction or inhibition of bioburden.

In certain embodiments, a tissue treatment product that has been functionalized with one or more desired metal-binding protein is implanted in a patient and provides for the targeted delivery of that protein to the site of implantation. The implanted tissue treatment product can be functionalized with any desired metal-binding protein that will provide beneficial effects following implantation of the tissue treatment product.

For example, the metal-binding protein can provide antimicrobial properties, thereby reducing or inhibiting the bioburden on the implanted tissue treatment product. In certain embodiments, the implanted tissue treatment product that is functionalized with an antimicrobial protein has, at any point in time following implantation into a host tissue, at least a 5, 10, 15, 20, 25, 30, 35, 40, 45, 50, 55, 60, 65, 70, 75, 80, 85, 90, 95, 96, 97, 98, or 99% (or any percentage in between) lower concentration of microorganisms growing on the product, as compared to implanted tissue treatment product that is not functionalized with an antimicrobial protein. For example, the tissue treatment product can be functionalized with lysostaphin, a zinc-binding peptidase that can cleave the cell walls of certain strains of staphylococci, such as *S. aureus*. Effective concentrations of the antimicrobial agent, such as lysostaphin, will vary depending on the type of agent used and the desired reduction in bioburden. Methods of determining effective concentration are known to one of skill in the art and include, e.g., measuring differences in bioburden following implantation of tissue treatment products containing different concentrations of antimicrobial proteins, or deliberate bacterial infection at the site of implantation and subsequent measurement of bioburden on implanted tissue treatment products containing different concentrations of antimicrobial proteins.

In some embodiments, a tissue treatment product having antimicrobial properties is prepared by contacting the tissue treatment product with a solution containing a high enough concentration of metal such that the metal that binds to the functionalized tissue treatment product will be sufficient to produce a reduced bioburden. In certain embodiments, a sufficient concentration of metal is achieved by contacting the tissue treatment product with a solution containing the metal at a concentration of at least about 0.5, 1.0, 1.5, 2.0 mM (or any concentration in between). In some embodiments, the metal is zinc and is present in solution at a concentration of at least about 0.5, 1.0, 1.5, 2.0 mM (or any concentration in between).

In another example, a tissue treatment product can be functionalized with one or more matrix metalloproteinases, which are important for regulation of cell proliferation, migration, differentiation, angiogenesis, and inflammation. In certain embodiments, the one or more matrix metalloproteinases promote or enhance tissue treatment, repair, and/or regeneration.

In certain embodiments, implanting a tissue treatment product provides a biocompatible scaffold that supports the native tissue migration, proliferation, and/or vascularization necessary for tissue regeneration, repair, healing, and/or treatment and does not elicit a substantial immune response that prevents such activity. As used herein, a "substantial immune response" is one that prevents partial or complete tissue regeneration, repair, healing, or treatment. In certain embodiments, the implanted tissue treatment product lacks certain undesirable antigens in order to avoid inducing an immune response. For example, in some embodiments, the implanted tissue treatment products lack substantially all α-gal moieties that are known to elicit reactions in humans.

In certain embodiments, the tissue treatment products that are implanted in a patient comprise human or animal tissue that is completely or substantially free of all cells normally present in the tissue from which the tissue treatment product is derived. As used herein, "substantially free of all cells" means that the tissue treatment product contains less than 20%, 10%, 5%, 1%, 0.1%, 0.01%, 0.001%, or 0.0001% (or any percentage in between) of the cells that normally grow within the acellular matrix of the tissue prior to decellularization.

In some embodiments, the implanted tissue treatment products can include extracellular scaffolds that have been repopulated with viable cells. Various cell types can be used for repopulation, including stem cells such as embryonic stem cells, adult stem cells (e.g. mesenchymal stem cells), and/or neuronal cells. Any other viable cells can also be used. In some embodiments, the cells are mammalian cells. Such cells can promote native tissue migration, proliferation, and/or vascularization. In various embodiments, the viable cells are applied to the acellular tissue matrix before or after implantation of a tissue treatment product.

In certain embodiments, implanted tissue treatment products further comprise one or more additional agents. In some embodiments, the additional agent can comprise an anti-inflammatory agent, an analgesic, or any other desired therapeutic or beneficial agent that promotes tissue repair, regeneration, or treatment following implantation. In certain embodiments, the additional agent can comprise, e.g., at least one added growth or signaling factor (e.g., a cell growth factor, an angiogenic factor, a differentiation factor, a cytokine, a hormone, and/or a chemokine). These additional agents can promote native tissue migration, proliferation, and/or vascularization.

Tissue treatment products can be implanted in a patient as part of any medical procedure in which tissue repair, regeneration, or treatment is desired. For example, tissue treatment products can be implanted following the creation of space between tissue planes as a result of disease, trauma, or surgical intervention. In some embodiments, the product can be implanted into a space between separated tissue planes and folded, compressed, or otherwise molded to fill the anatomical shape of the implant site. In various embodiments, the implanted product can provide a scaffold for native tissue migration, proliferation, and/or revascularization. In addition, in certain embodiments, chelating agents, metals and/or metal-binding proteins on tissue treatment products can be delivered directly to the surrounding native tissue following implantation via direct physical contact.

In another example, tissue treatment products can be used as tissue fillers by implanting them following the removal of bulk soft tissue from a patient, e.g., tumor removal. It has been shown that after tumor removal, tissue re-growth is generally poor, especially as to the subcutaneous tissue layers. Generally, a layer of skin will regrow after tumor removal, but the underlying tissue remains unregenerated. Thus, in various embodiments, tissue treatment products can be used as implants to replace bulk soft tissue after tumor removal. In certain embodiments, such implants serve as tissue fillers that can provide structural integrity to the remaining tissue at the implant site. In certain embodiments, where the bulk tissue that is removed is near or includes the skin, implantation of a tissue treatment product can provide the implant site with a more natural look and/or feel after tumor removal. In various embodiments, the implanted product can also provide a scaffold for native tissue migration, proliferation, and revascularization. In addition, in certain embodiments, chelating agents, metals and/or metal-binding proteins on tissue treatment products can be delivered directly to the surrounding native tissue following implantation via direct physical contact.

In yet another example, tissue treatment products can be used for aesthetic purposes, e.g., as implants or in conjunction with traditional implants. For example, tissue treatment products can be used to support traditional breast implants, e.g., for use in breast augmentation and/or reconstruction. For example, a tissue treatment product can be placed around a breast implant and used to fill the space between the implant and surrounding native tissue, thereby providing a smoother contour and/or more natural look and feel for the implant. At the same time, in certain embodiments, the implanted tissue treatment product can provide a scaffold into which cells from native tissue surrounding the breast implant can grow and proliferate, thereby more firmly securing the breast implant in place and/or reducing the amount of undesirable fibrosis that develops around the implant. In addition, in certain embodiments, chelating agents, metals and/or metal-binding proteins on tissue treatment products can be delivered directly to the surrounding native tissue following implantation via direct physical contact.

EXAMPLES

The following examples serve to illustrate, and in no way limit, the present disclosure.

Example 1: Antimicrobial Activity of Lysostaphin-Treated Acellular Dermis

Figure 2:
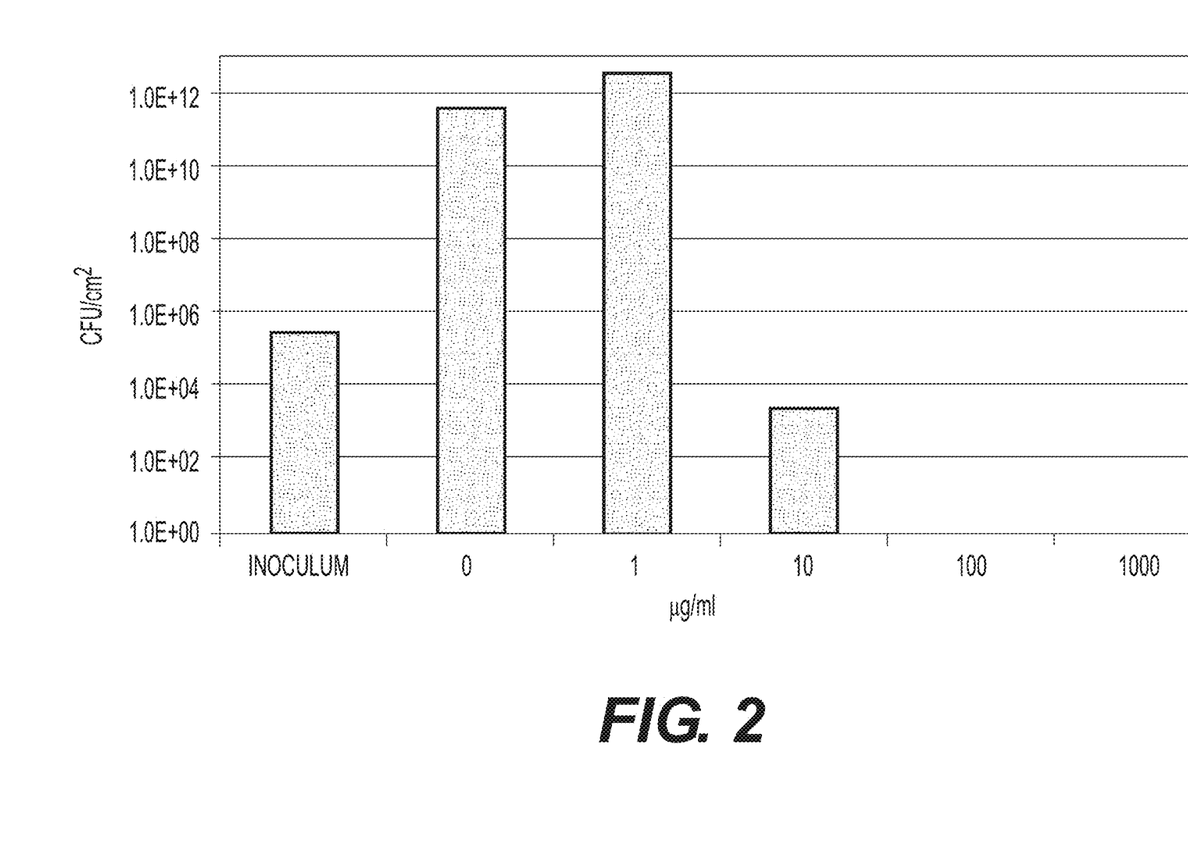
FIG. 2 shows bacterial colony forming units (CFUs) as a function of the concentration (µg/ml) of lysostaphin in saline solution coated on acellular porcine dermal samples after an overnight incubation with approximately $1E^{\wedge}6$ S. aureus at 37° C.

Samples of acellular porcine dermal tissue (1.5 cm×1.5 cm) were incubated with lysostaphin in a saline solution at the concentrations (μg/ml) indicated in FIG. 2 for 3 hours at room temperature. Tissue samples were then rinsed with saline and placed on a tryptic soy agar plate. A solution containing approximately 1e^6 cells of *S. aureus* were inoculated onto the tissue, which were incubated overnight at 37° C. The following morning, the bacterial concentration (CFU) on each tissue sample was determined following extraction and serial dilution of the bacteria growing on the tissue samples. FIG. 2 shows that antimicrobial activity, as indicated by a reduction in bacterial CFU, was achieved using lysostaphin concentrations of 10 μg/ml or higher.

Example 2: Antimicrobial Activity of Zinc-Immobilized Lysostaphin

50 μl samples of iminodiacetic acid-agarose were incubated in a saline solution either containing zinc or lacking zinc (control). The samples were then washed three times with saline to remove unbound zinc prior to incubating the samples with solutions containing the concentrations of lysostaphin indicated in Table 1. After incubation, samples were washed three times with saline and 100 μl of a saturated culture of *S. aureus* was added to each sample. Following a 1 hour incubation at room temperature, Alamar blue was added to screen for viable bacteria. A pink color indicated viable bacteria, while blue indicated that the majority of the bacteria were no longer viable. Table 1.

TABLE 1

Antimicrobial Activity of Lysostaphin Captured on IDA-Agarose

| Lysostaphin | No Zinc | Zinc |
|---|---|---|
| 1 ug/ml | Viable | Non-viable |
| 5 ug/ml | Viable | Non-viable |
| 10 ug/ml | Viable | Non-viable |
| 20 ug/ml | Viable | Non-viable |

Table 1 shows that antimicrobial activity, as indicated by a majority of non-viable bacteria on an agarose sample, was achieved in samples treated with at least 1 μg/ml lysostaphin.

Example 3: Antimicrobial Activity of IDA-Zinc Functionalized Acellular Dermis

Figure 3:
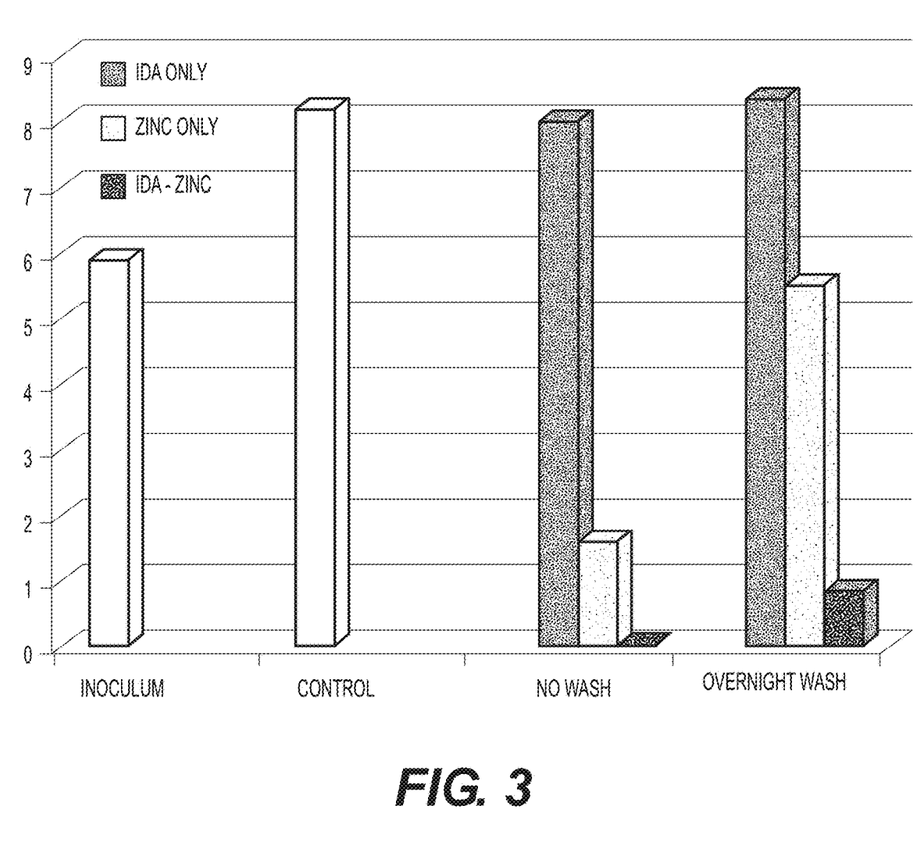
FIG. 3 shows bacterial concentration (CFU, plotted on a logarithmic scale) after an overnight incubation with approximately $1E^{\wedge}6$ S. aureus at 37° C. for tissue matrices functionalized with IDA only, with zinc only, or with IDA and zinc, as well as for control samples and for inoculums samples. CFU measurements are shown for tissue matrices inoculated with S. aureas after functionalization, as well as for tissue matrices inoculated with S. aureas after functionalization and an overnight wash in saline.

Acellular porcine dermal tissue samples (1 cm×1 cm) were incubated in the presence of 1 mM NHS-IDA for 4 hrs. Samples were then washed with saline and incubated in a 1 mM zinc sulfate solution. Some samples were then rinsed in saline overnight to remove excess/unbound zinc. Tissue samples were placed on a tryptic soy agar plate and inoculated with a solution containing approximately 1e^6 cells of *S. aureus*. After an overnight incubation at 37° C., the bacterial concentration (CFU) on each tissue sample was determined following extraction and serial dilution of the bacteria growing on the tissue samples. FIG. 3 shows that zinc functionalized and IDA-zinc functionalized acellular dermal tissue matrices had reduced bacterial concentrations, as compared to control samples and IDA-only samples.

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:
1. A tissue treatment product for inhibiting growth of *S. aureus* comprising:
   a porous material comprising a natural or artificial scaffold, wherein the porous material comprises at least one of an extracellular matrix of a partially decellularized tissue, an extracellular matrix of a completely decellularized tissue, and a porous synthetic scaffold material, wherein the extracellular matrix of a partially or completely decellularized tissue is selected from at least one of human, nonhuman primate, pig, cow, horse, goat, sheep, dog, cat, rabbit, guinea pig, gerbil, hamster, rat, and mouse tissue;

at least one chelating agent selected from the group consisting of iminodiacetic acid (IDA), nitrilotriacetic acid (NTA), ethylenediaminetetraacetic acid (EDTA), or diethylenetriaminepentaacetic acid (DTPA) covalently bound to the porous material; and zinc bound to the chelating agent(s) on the tissue treatment product.

2. The tissue treatment product of claim 1, wherein the tissue treatment product comprises a porous synthetic scaffold material.

3. The tissue treatment product of claim 1, wherein the tissue treatment product comprises at least one of a hyaluronic acid derivative, chitosan, polycaprolactone, polyglycolide, polylactide, polydioxane, a polyether ester, poly(lactide-co-glycolide), or polyhydroxyalkonate.

4. The tissue treatment product of claim 1, wherein the tissue treatment product comprises a polyurethane material.

5. The tissue treatment product of claim 1, wherein the extracellular matrix is partially or completely decellularized pig tissue.

6. The tissue treatment product of claim 1, wherein the tissue treatment product comprises the extracellular matrix of partially or completely decellularized tissue selected from at least one of bone, skin, dermis, intestine, vascular, urinary bladder, tendon, ligament, muscle, fascia, neurologic tissue, vessel, liver, heart, lung, kidney, and cartilage tissue.

7. The tissue treatment product of claim 1, wherein the tissue treatment product comprises an extracellular matrix from one or more animal or tissue sources.

8. The tissue treatment product of claim 1, wherein the tissue treatment product lacks substantially all alpha-galactose moieties.

9. The tissue treatment product of claim 1, further comprising one or more viable cells.

10. The tissue treatment product of claim 9, wherein the one or more cells are mammalian cells.

11. The tissue treatment product of claim 9, wherein the one or more cells are stem cells.

12. The tissue treatment product of claim 1, further comprising at least one factor selected from an anti-inflammatory agent, an analgesic, a cell growth factor, an angiogenic factor, a differentiation factor, a cytokine, a hormone, and a chemokine.

13. The tissue treatment product of claim 12, wherein the at least one factor is encoded by a nucleic acid sequence contained within an expression vector.

14. The tissue treatment product of claim 13, wherein the expression vector is contained within one or more viable cells.

15. The tissue treatment product of claim 1, wherein the tissue treatment product has a reduced bioburden or substantially lacks all bioburden.

16. The tissue treatment product of claim 1, wherein the at least one chelating agent is covalently bound to free amine, thiol, or hydroxyl groups on the porous material in the tissue treatment product.

17. The tissue treatment product of claim 1, wherein the at least one chelating agent is covalently bound to the porous material in the tissue treatment product via an activating agent.

18. The method of claim 17, wherein the activating agent is N-hydroxysulfosuccinimide (NHS), suberic acid bis(N-hydroxysuccinimide ester), 1,4-butanediol diglycidyl ether, epibromohydrin, or 1,2,7,8-diepoxyoctane.

19. The tissue treatment product of claim 1, wherein the chelating agent comprises IDA.

20. The tissue treatment product of claim 1, further comprising at least one metal in addition to zinc.

21. The tissue treatment product of claim 1, wherein the tissue treatment product is further functionalized with at least one metal-binding protein.

22. The tissue treatment product of claim 21, wherein the metal-binding protein has antimicrobial properties.

23. The tissue treatment product of claim 21, wherein the metal-binding protein comprises lysostaphin.

24. The tissue treatment product of claim 21, wherein the metal-binding protein comprises at least one matrix metalloproteinase.

25. The tissue treatment product of claim 24, wherein the matrix metalloproteinase comprises a collagenase, gelatinase, stromolysin, matrilysin, or elastase.

26. The tissue treatment product of claim 1, wherein the tissue treatment product comprises a porous material covalently bound to IDA and functionalized with zinc and lysostaphin.

27. A kit comprising the tissue treatment product of claim 1 and instructions for using the kit.

28. The kit of claim 27, wherein the kit is packaged under aseptic or sterile conditions.

* * * * *